United States Patent

Suzuki et al.

[11] Patent Number: 5,906,824
[45] Date of Patent: May 25, 1999

[54] ANTITHROMBOGENIC MATERIAL AND METHOD FOR PRODUCING THE SAME

[75] Inventors: Yoshiaki Suzuki; Aiko Nakao; Masaya Iwaki, all of Saitama; Masahiro Kusakabe, Kanagawa; Hiroshi Nakajima, Tokyo; Sanzo Kaneko, Kanagawa; Hiroyuki Honda, Tokyo, all of Japan

[73] Assignees: Sony Corporation, Tokyo; The Institute of Physical and Chemical Research, Saitama, both of Japan

[21] Appl. No.: 08/856,751

[22] Filed: May 15, 1997

[30] Foreign Application Priority Data

May 17, 1996 [JP] Japan .................................. 8-123475

[51] Int. Cl.$^6$ .................................................. R01N 25/34
[52] U.S. Cl. ........................................ 424/402; 424/400
[58] Field of Search ...................... 424/402, 400

[56] References Cited

U.S. PATENT DOCUMENTS 3,625,745  12/1971  Wright et al. ......................... 117/93.31
5,028,597   7/1991  Kodama et al. .......................... 514/56
5,152,783  10/1992  Suzuki et al. ................................ 623/1

*Primary Examiner*—Jose G. Dees
*Assistant Examiner*—Kathryne E. Shelborne
*Attorney, Agent, or Firm*—Hill & Simpson

[57] ABSTRACT

An antithrombogenic material whose stickiness to cells is maintained but whose stickiness to blood platelet is inhibited, is disclosed, which comprises a substrate and a biopolymer material coated on said substrate, the antithrombogenic material being obtained by irradiating the biopolymer material with ion beam to maintain its stickiness to a cell but reduce its stickiness to a blood platelet. In accordance with the present invention, there is also provided a method for producing the antithrombogenic material.

9 Claims, 2 Drawing Sheets

ANTITHROMBOGENIC MATERIAL AND METHOD FOR PRODUCING THE SAME

BACKGROUND OF THE INVENTION

1. Field of the Invention

The present invention relates to an antithrombogenic material having a reduced stickiness to blood platelet, and a method for producing the antithrombogenic material.

2. Prior Art

In recent years, there has been a positive tendency that cell-embedded type hybrid artificial organs are applied to organs such as cutis, mucosa, blood vessel, liver, spleen or the like, whose functions cannot be sufficiently attained only by using substitute products made of an artificial material. Also, the development of biosensors, switching devices, bioreactors or the like, which utilize cells, have increasingly proceeded.

In the development of these devices, it has been an important task to select and design a matrix material serving as a support for cells to be cultivated. For instance, if blood platelet is adhered on a surface of the matrix material and thrombus is formed by the coagulation thereof, it becomes impossible to apply the matrix material to the aforementioned artificial organs, especially artificial blood vessel. That is, in the case where the matrix material is used to produce artificial organs or the like, it is inevitably required to control its stickiness to blood platelet in order to realize artificial organs having a high performance.

As conventional materials having a reduced stickiness to the blood platelet (hereinafter referred to as an "antithrombogenic material"), a polymer material to which heparin is bonded, a polymer material on which urokinase is fixed, a block copolymer of hydroxyethyl methacrylate with styrene or the like are exemplified. However, these polymer materials as antithrombogenic materials serve for reducing stickiness not only to the blood platelet but also to cells.

As described above, since the above-mentioned conventional antithrombogenic materials have reduced stickiness to both blood platelet and cells, it has been difficult to apply these materials to cell-embedded-type hybrid artificial organs due to poor adhesion to cells.

On the other hand, conventionally, as materials having reduced stickiness to blood platelet while maintaining stickiness to cells, there are known those produced by chemically modifying biopolymer proteins such as collagen. Specifically, Japanese Patent Application Laid-open No. Sho-58-165854 discloses a method in which blood compatibility of collagen and pseudo-formation of intima thereby are improved by succinylating amino groups (—NH$_2$) as side chains in polypeptide chain of collagen.

In the method disclosed in the Japanese Patent Application, the biopolymer material having stickiness to cells is chemically inhibited from exhibiting stickiness to blood platelet.

The material described in the afore-mentioned Japanese Patent Application Laid-open No. Sho58-165854 is prepared by chemically modifying the amino groups as side chains in the polypeptide chain. However, since the chemical reaction for the chemical modification of the amino groups is difficult to control, the biopolymer material cannot be uniformly subjected to the chemical modification. For this reason, conventional antithrombogenic materials are not satisfactory in anti-thrombogenic property and stickiness to cells. Accordingly, there arises a problem that the conventional antithrombogenic materials have only a low reliability with respect to the anti-thrombogenic property and the stickiness to cells.

Further, the method disclosed in the afore-mentioned Japanese Patent Application Laid-open No. Sho58-165854 is associated with poor controllability of the chemical reaction in which the amino groups in the polypeptide chain are chemically modified, and complicated manufacturing processes. This leads to the difficulty in producing antithrombogenic materials having uniform anti-thrombogenic property and stickiness to cells.

The present invention has been accomplished in view of the afore-mentioned problems encountered in the prior art.

SUMMARY OF THE INVENTION

Accordingly, it is an object of the present invention to provide an antithrombogenic material having satisfactory stickiness to cells but sufficiently inhibited from exhibiting stickiness to blood platelet, and having a high reliability.

It is another object of the present invention to provide a method for producing such an antithrombogenic material.

As a result of various studies made by the present inventors to accomplish the afore-mentioned objects, it has been unexpectedly found that the biopolymer having a good stickiness to cells, such as gelatin or collagen, loses the stickiness to blood platelet by irradiating ion beam thereto. Further, it has been found that by appropriately selecting conditions such as kind, acceleration energy and amount of ion beam irradiated, the biopolymer can be controlled so as to reduce only the stickiness of the biopolymer to blood platelet.

In a first aspect of the present invention, there is provided an antithrombogenic material comprising a substrate and a biopolymer material coated on said substrate, the antithrombogenic material being obtained by irradiating the biopolymer material with ion beam to maintain its stickiness to a cell but reduce its stickiness to a blood platelet.

In a second aspect of the present invention, there is provided a method for producing an antithrombogenic material composed of a substrate and a biopolymer material coated thereon, comprising the step of irradiating ion beam onto the biopolymer material coated on the substrate, the irradiated ion beam having an acceleration energy of 50 to 150 kev and containing $1 \times 10^{14}$ to $1 \times 10^{17}$ ions per cm$^2$.

DETAILED DESCRIPTION OF THE INVENTION

According to the experiments made by the present inventors, it has been ascertained that gelatin or collagen coated on a polystyrene substrate was provided with a surface portion exhibiting non-stickiness to blood platelet when subjected to a so-called ion implantation method, i.e., when irradiated with ion beam such as O$^+$, Ne$^+$, Na$^+$, Ar$^+$, K$^+$ or the like.

In this case, the surface portion exhibiting non-stickiness to blood platelet can be constituted by fibronectin, laminin and vitronectin in addition to the afore-mentioned collagen or gelatin.

The acceleration energy of the ion beam irradiated may be in the range of 50 to 150 keV, and the amount (number) of ion beam irradiated may be in the range of $1\times10^{14}$ to $1\times10^{17}$ ions per $cm^2$.

Especially, when $He^+$ ion beam having an acceleration energy of 150 keV is irradiated in an amount of $1\times10^{14}$ to $1\times10^{17}$ ons per $cm^2$, the biopolymer can have a surface portion which is inhibited from exhibiting stickiness to blood platelet but can maintain stickiness to cells.

Such a phenomenon has not been reported at all until now and has been first found by the present inventors.

In the afore-mentioned antithrombogenic material and the afore-mentioned method for producing the antithrombogenic material according to the present invention, when cell-stickiness of the biopolymer material such as collagen or gelatin which are known as an extracellular matrix, is destroyed by irradiating ion beam to only a site thereof which is in contact with blood platelet, the surface portion exhibiting inhibited stickiness to blood platelet can be formed thereon.

Especially, by appropriately selecting kind, acceleration energy and amount of ion beam irradiated, only the site being in contact with blood platelet among the portion having stickiness to cells is destroyed so that the biopolymer can be formed with a surface exhibiting only stickiness to cells.

In the following, preferred embodiments of the present invention are described in detail by referring to specific experimental results.

Structure of Ion Implantation Apparatus

Figure 1:
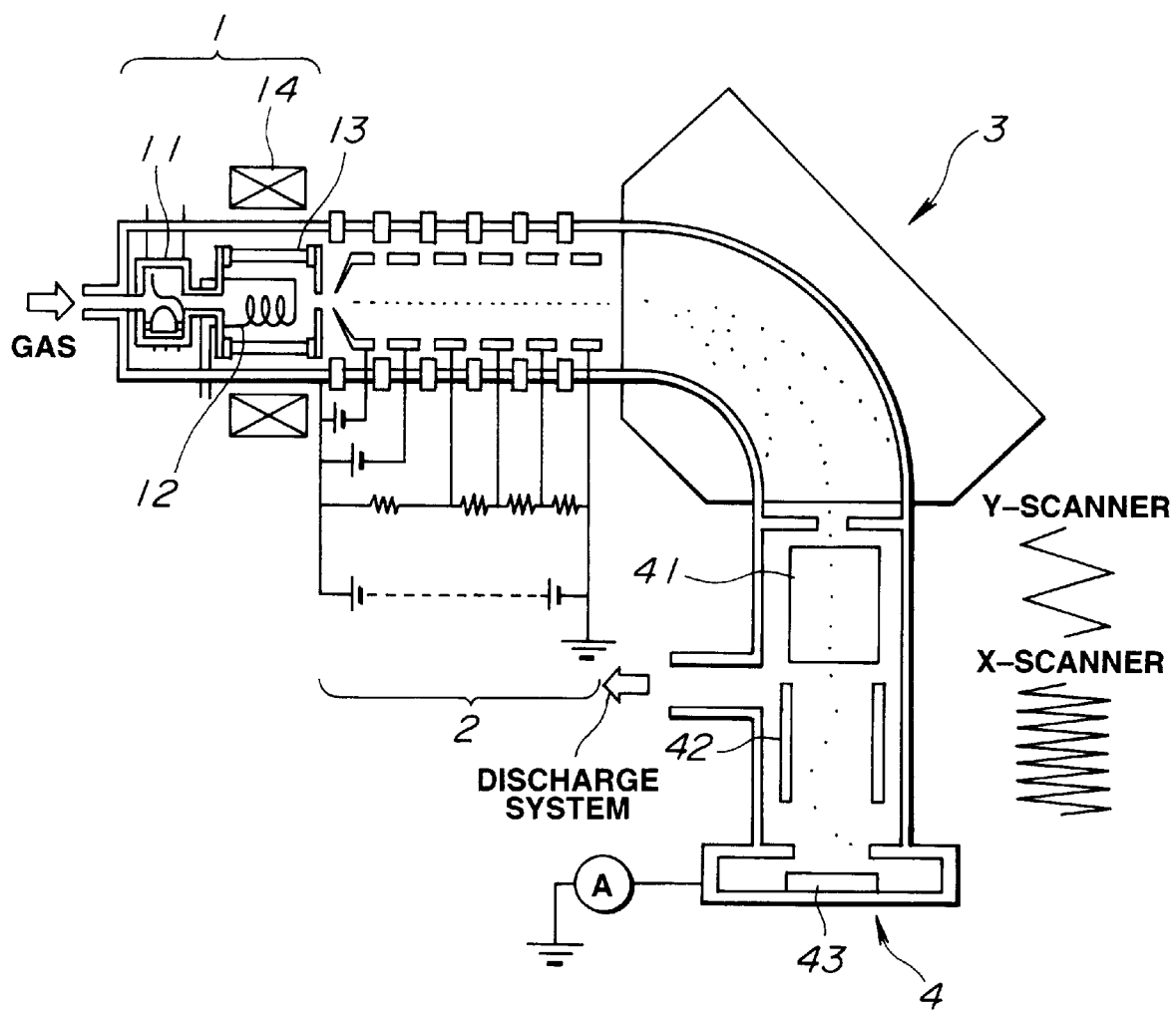
FIG. 1 is a view schematically showing an example of an ion implantation apparatus.

FIG. 1 schematically shows an ion implantation apparatus which can be used in a preferred embodiment of the present invention. The ion implantation apparatus is of a so-called front-stage acceleration type which is constituted by an ion source 1 from which the aimed ion is generated by ionization, an acceleration system 2 for accelerating the ion generated, a mass separation system for separating the aimed ion from the remainder, and a target chamber into which the ion is irradiated toward a target.

The ion source 1 includes an oven 11, a filament (cathode) 12, an anode 13, a coil 14 and the like. An appropriate material accommodated in the oven 11 is gasified to generate plasma of desired ion.

The afore-mentioned acceleration system 2 includes leading electrodes, focus electrodes or the like. The ion beam is caused to have a required energy while passing therethrough.

Further, the mass separation system 3 includes a magnet which serves for diverting a flow direction of the ion beam by 90 degrees, thereby selectively removing impurity ions from the desired ions by utilizing a difference in locus therebetween which in turn is based on a difference in mass therebetween.

On the other hand, a Y-scanner (deflecting electrode) 41 and an X-scanner are disposed between the mass separation system 3 and the target chamber 4. These scanners electrically raster-scans the ion beam entering from the mass separation system 3, thereby enabling uniform ion implantation relative to a target 43 placed in the target chamber 4. Incidentally, the target 43 placed in the target chamber 4 is a specimen using a tubular substrate as described in detail hereinafter.

The ion implantation method using the afore-mentioned ion implantation apparatus has such features that a single ion beam having an extremely high purity can be obtained due to the provision of the mass separation system 3, and that the ion beam has a kinetic energy as high as 50 keV or more.

Specimen

In the preferred embodiment of the present invention, the specimen is constituted by a tubular substrate as described above. As the tubular substrate, for example, a polystyrene tube (PS tube) having an inner diameter of 2 mm or a stretched polytetrafluoroethylene tube (ePTFE tube) having an inner diameter of 3 mm can be used. In the specimen according to the preferred embodiment of the present invention, collagen or gelatin as a biopolymer material is coated on an inner surface of the PS tube or the ePTFE tube.

The afore-mentioned tubular substrate may be made of other materials such as glass or metal in addition to polystyrene and polytetrafluoroethylene. Further, in the preferred embodiment of the present invention, as the biopolymer materials, there may be used other biopolymer materials having stickiness to cells, such as fibronectin, laminin, vitronectin or the like as well as the aforementioned collagen and gelatin.

Method for Irradiating Ion Beam

In the preferred embodiment of the present invention, the specimen prepared in the afore-mentioned manner is irradiated with ion beam by means of the ion implantation apparatus having the afore-mentioned construction. At this time, while the tubular specimen is maintained in an inclined state by using a goniometer as shown in FIG. 2, the ion beam is irradiated to collagen or gelatin coated on the inner surface thereof.

Figure 2:
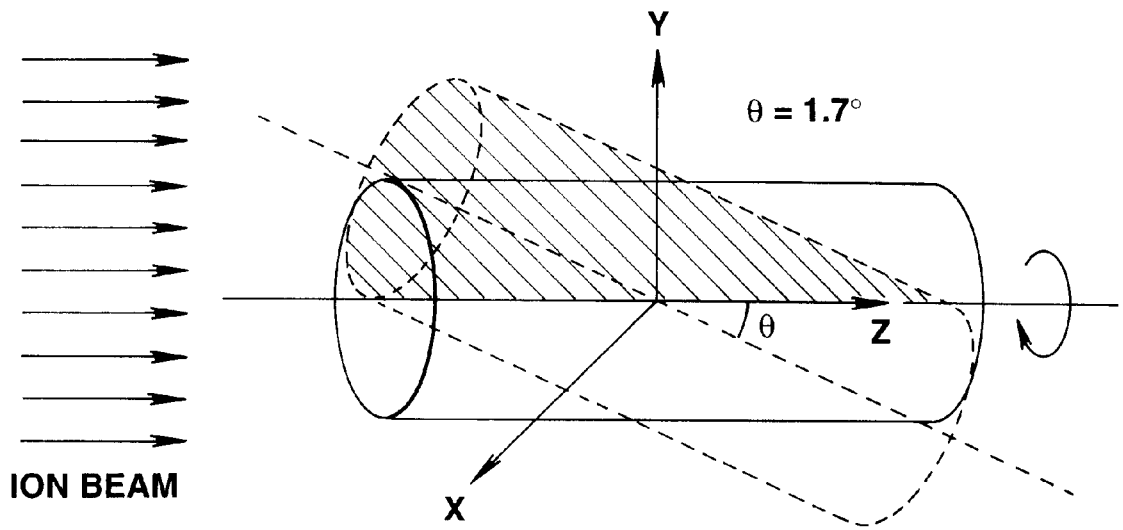
FIG. 2 is a view schematically showing conditions of a specimen mounted in the ion implantation apparatus.

Specifically, the tubular specimen is disposed in such a manner that a center axis Z thereof is inclined by ±1.7 degrees within a vertical plane YZ relative to a horizontal plane XZ as indicated by a dotted line in FIG. 2. While maintaining the tubular specimen in the afore-mentioned condition, the ion beam is irradiated to the specimen from opposite sides. Further, the tubular specimen is caused to rotate about the center axis Z by 90 degrees while irradiating the ion beam thereto in the afore-mentioned manner.

First, the tubular specimen is rotated to such a position that the center axis Z is inclined by −1.7 degrees within the vertical plane YZ relative to the horizontal plane XZ, and then irradiated with the ion beam from opposite sides thereof.

Next, the tubular specimen is rotated to such a position that the center axis Z is inclined by +1.7 degrees within the vertical plane YZ relative to the horizontal plane XZ, and then irradiated with the ion beam from opposite sides thereof.

By these treatments, the layer of collagen or gelatin coated over the inner surface of the specimen can be uniformly irradiated as a whole with the ion beam.

EXAMPLES

The present invention is described in detail below by way of examples. Experimental Example 1
Experiment for evaluating antithrombogenic property An experiment for evaluating an anti-thrombogenic property of the specimen was conducted by using the ion implantation apparatus as shown in FIG. 1. The ion beam of $He^+$, $Ne^+$, $Na^+$, $Ar^+$ or $K^+$ having an acceleration energy of 150 keV was irradiated to the inner surface of the specimen in an amount (number) of $1\times10^{14}$ to $1\times10^{17}$ ions per $cm^2$ in the afore-mentioned manner. The thus-treated tubular specimen was internally substituted for a femoral artery and a femoral vein of a mongrel adult dog as a subject, and then observed with respect to the condition of the inner surface thereof. Further, in a long-term experiment, the tubular specimen was observed with respect to the inner surface thereof 17 days and 30 days after it was internally substituted for a carotid artery of the dog.

The tubular substrate used in Experimental Example 1 was a PS tube on which the biopolymer material was coated. Specifically, the inner surface of the tubular substrate was coated with four kinds of biopolymer materials including collagen, fibronectin, laminin and vitronectin.

In Experimental Example 1, after the thus-formed specimen was held in place, a flow rate of blood was measured with time by means of an electromagnetic flow-meter fixed on a peripheral side of the blood vessel. Further, the specimen was removed from the subject at predetermined intervals at each time of which the inner surface thereof was washed with a heparin-containing physiological salt solution and thereafter visually observed as to whether or not any thrombus is formed thereon. Furthermore, the inner surface of the specimen was observed by means of a scanning electron microscope to ascertain whether or not any blood platelet is adhered thereto.

The opening conditions of the inner surface of the respective specimens whose anti-thrombogenic properties were tested and evaluated above, are shown in Table 1.

TABLE 1

| Retention time in organs | Femoral artery | Femoral vein | Carotid artery |
| --- | --- | --- | --- |
| 1 hour | Still opened | Still opened | — |
| 2 hours | Still opened | Still opened | — |
| 2.5 hours | Still opened | Still opened | — |
| 4.5 hours | Still opened | Still opened | — |
| 24 hours | Still opened | Still opened | — |
| 17 days | — | — | Still opened |
| 30 days | — | — | Still opened |

As will be apparently understood from Table 1, was confirmed that both the specimens still had an opened inner surface even after they were indwelled in the femoral artery and femoral vein for the afore-mentioned period of time. In addition, when the stickiness of the respective specimens to blood platelet was observed by means of a scanning electron microscope, it was confirmed that a slight amount of blood platelet was interspersed on the inner surface of each specimen but no pseudopodium-like projections were produced by the adhesion of blood platelet. The inner surface of the specimen, which was internally substituted for the carotid artery, was still kept in opened state even after 17 days to 30 days. This indicated that the specimen had a good anti-thrombogenic property.

As will be appreciated from the above results, the anti-thrombogenic material according to the present invention had no stickiness to blood platelet even after 24 hours and therefore exhibited a good anti-thrombogenic property.

Comparative Example 1

The same procedure as described in Experimental Example 1 was carried out except that the specimens were not irradiated with ion beam. The opening conditions of the inner surface of the respective tested specimens are shown in Table 2 below.

TABLE 2

| Retention time in organs | Femoral artery | Femoral vein |
| --- | --- | --- |
| 20 minutes | Occluded | Occluded |
| 30 minutes | Occluded | Occluded |
| 1 hour | Occluded | Occluded |

As is apparent from Table 2, the inner surfaces of both the specimens indwelled in the femoral artery and femoral vein were occluded only after a retention time of 20 minutes elapsed. In addition, when the specimen of Comparative Example 1 was observed by means of a scanning electron microscope, it was confirmed that blood platelet was adhered onto the inner surfaces of the specimens and that the fibrin network was produced thereon.

As is apparently appreciated from the above results, in the case where the specimens are not irradiated with ion beam, the thrombus is produced on the specimens so that the blood circulation is considerably inhibited.

Experimental Example 2

Test for evaluating stickiness to cells

In this Experimental Example 2, as a specimen, there-was used a petri dish which was coated with collagen. The ion beam having an acceleration energy of 150 keV was irradiated onto the surface of the specimen in an amount of $1 \times 10^{14}$ to $1 \times 10^{17}$ ions per $cm^2$. A culture solution (Tradename "RPMI-1640" manufactured by Nissui Yakuhin Co., Ltd.) containing 10% of a bovine serum and $8 \times 10^4$ cells/ml of blood vessel endothelium derived from a bovine aorta was added to the thus-treated specimen. The specimen was observed by means of a phase-contrast microscope with respect to its stickiness to the bovine vessel endothelium.

Comparative Example 2

Figure 3:
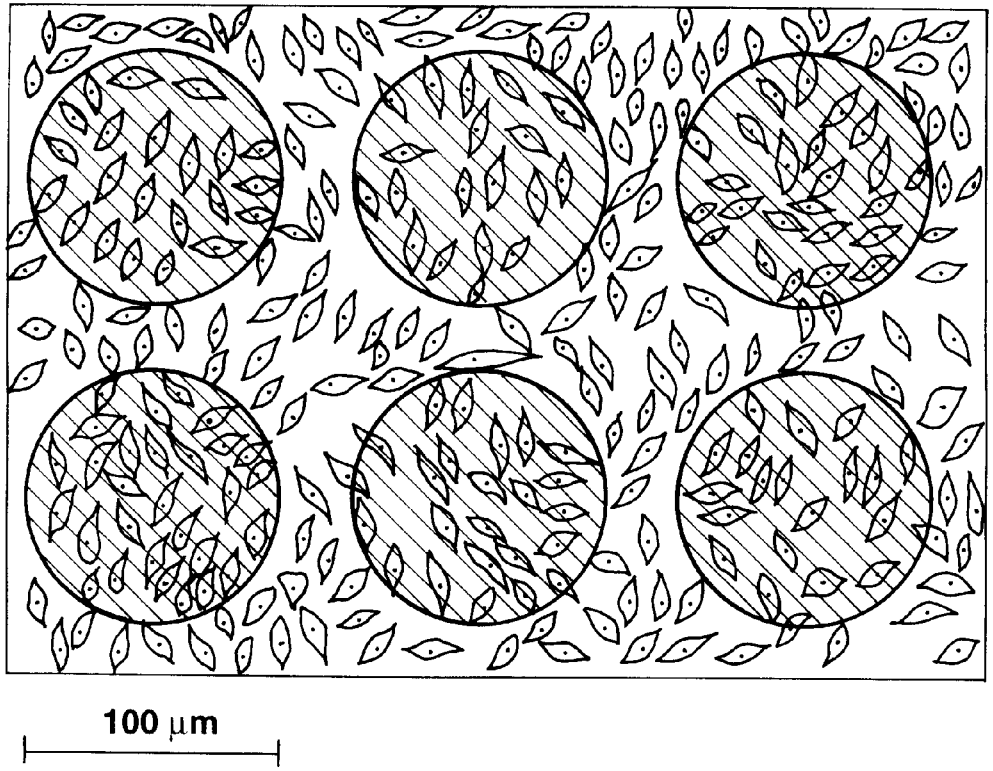
FIG. 3 is a view schematically showing cell-adhesion conditions on the specimen which has the ion beam-irradiated portions and the non-irradiated portions.

The same procedure as described in Experimental Example 2 was carried out except that the ion beam was irradiated onto only circular portions of the specimen such that a region which was not irradiated with the ion beam, remained thereon. At that time, it was confirmed that blood vessel endothelium was adhered to both the irradiated and non-irradiated portions to a similar extent, as shown in FIG. 3.

As will be apparently understood from the above results, when the ion beam is irradiated onto the specimens coated with the biopolymer material, the specimens are not inhibited from adhering to cells, i.e., the stickiness to cells is still maintained after the irradiation. Incidentally, as a matter of course, the biopolymer material coated onto the petri dish is not limited to collagen, but may also include those biopolymer materials exhibiting an adhering property to cells, such as gelatin, fibronectin, laminin, vitronectin or the like.

As is apparently appreciated from Experimental Examples 1 and 2 mentioned above, the antithrombogenic material according to the present invention can exhibit an inhibited stickiness to blood platelet while maintaining a adhesion property to cells. Further, the antithrombogenic material can have a good anti-thrombogenic effect based on the inhibited stickiness to blood platelet. Furthermore, since the antithrombogenic material can maintain the stickiness to cells, it is possible to incubate or cultivate cells which are adhered to a surface thereof. Accordingly, the antithrombogenic material is useful for producing cell-embedded type hybrid artificial organs which have to be used within a body for a long period of time.

As is apparent from the above discussion, in accordance with the present invention, it is possible to provide an antithrombogenic material whose stickiness to blood platelet is highly inhibited but whose stickiness to cells is sufficiently maintained, thereby exhibiting a high reliability. Accordingly, such an antithrombogenic material according to the present invention is extremely useful in developments of biosensors, switching devices, bioreactors or the like which cooperates with cells, as well as the afore-mentioned cell-embedded type hybrid artificial organs.

The antithrombogenic material according to the present invention is expected to be utilized in the following applications.

1) Development of small-diameter artificial blood vessel

For example, in the case where occluded coronary artery is subjected to percutaneous coronary plastic surgery in catheter test or the like for early stage of acute myocardial infraction, the antithrombogenic material according to the present invention can be fitted on an inner surface of a small-diameter artificial blood vessel which is indwelled in the stenosed portion thereof. This can prevent not only occurrence of re-stenosis at the stenosed portion but also acute coronary occlusion which might be caused as a complication in the percutaneous coronary plastic surgery.

Also, for example, in an acute coronary occlusion caused due to dissociation of coronary artery as a grave complication resulting from the coronary artery plastic surgery, the antithrombogenic material according to the present invention can be fitted on an inner surface of the small-diameter artificial blood vessel which is inserted into the dissociated portion. This can ensure a simple flow of blood thorough the dissociated portion and can stabilize the blood circulation until an emergency operation is carried out.

2) Development of patches for curing damaged blood vessels

For example, in the case where blood vessels on which an aneurysm is formed or which suffers from arterial sclerosis are cured, the antithrombogenic material according to the present invention can be fitted onto an inner surface of the patch inserted into a blood vessel portion from which the damaged portion is removed by desection. The antithrombogenic material according to the present invention can realize a patch for curing damaged blood vessels which can exhibit an adhesion property to blood vessel endothelium but does not form a thrombus therein.

What is claimed is:

1. An antithrombogenic material comprising:
   a substrate; and
   a biopolymer material coated on said substrate,
   said antithrombogenic material being obtained by irradiating the biopolymer material with ion beam to maintain its stickiness to a cell but reduce its stickiness to a blood platelet.

2. An antithrombogenic material according to claim 1, wherein said biopolymer material is selected from gelatin, collagen, fibronectin, laminin and vitronectin.

3. A method for producing an antithrombogenic material composed of a substrate and a biopolymer material coated thereon, comprising the step of irradiating ion beam onto the biopolymer material coated on the substrate, said irradiated ion beam having an acceleration energy of 50 to 150 kev and containing $1\times10^{14}$ to $1\times10^{17}$ ions per $cm^2$.

4. A method according to claim 3, wherein said biopolymer material is selected from gelatin, collagen, fibronectin, laminin and vitronectin.

5. An antithrombogenic article comprising:
   a substrate having a blood contact surface;
   an applied layer of an ordinarily thrombogenic biopolymer material coated on said blood contact surface selected from the group consisting of gelatin, collagen, fibronectin, laminin and vitronectin, said applied layer having an exposed surface opposite the blood contact surface including a substantially non-thrombogenic surface portion comprising denatured biopolymer material, said substantially non-thrombogenic surface portion being obtained by irradiating the exposed surface of the applied layer with ion beam irradiation at from about $1\times10^{14}$ to about $1\times10^{17}$ ions/$cm^2$ at an acceleration energy of from about 50 to about 150 keV until said substantially nonthrombogenic surface portion is obtained.

6. An antithrombogenic article as defined in claim 5, wherein said substrate comprises a tubular substrate.

7. An antithrombogenic article as defined in claim 5, wherein said substrate comprises glass, metal, polystyrene or expanded polytetrafluoroethylene.

8. An artificial blood vessel comprising the antithrombogenic article defined in claim 5.

9. A patch for a damaged blood vessel comprising the antithrombogenic article defined in claim 5.

* * * * *